(12) United States Patent
Kodoi et al.

(10) Patent No.: US 7,193,106 B2
(45) Date of Patent: Mar. 20, 2007

(54) HALOGENOACETOXYADAMANTANE DERIVATIVES AND PROCESS FOR PRODUCTION THEREOF

(75) Inventors: Kouichi Kodoi, Chiba (JP); Shinji Tanaka, Chiba (JP); Toshihide Yoshitome, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 28 days.

(21) Appl. No.: 10/511,600

(22) PCT Filed: Apr. 28, 2003

(86) PCT No.: PCT/JP03/05442

§ 371 (c)(1),
(2), (4) Date: Jun. 10, 2005

(87) PCT Pub. No.: WO03/095413

PCT Pub. Date: Nov. 20, 2003

(65) Prior Publication Data

US 2005/0258395 A1  Nov. 24, 2005

(30) Foreign Application Priority Data

May 10, 2002  (JP) ............................. 2002-136183

(51) Int. Cl.
*C07C 69/03* (2006.01)
(52) U.S. Cl. ...................... 560/227; 560/228; 505/410; 505/413
(58) Field of Classification Search ................ 560/228, 560/227; 505/410, 413
See application file for complete search history.

(56) References Cited

U.S. PATENT DOCUMENTS 4,052,439 A * 10/1977 Herrin et al. ............... 560/129

4,134,991 A    1/1979   Wermuth

FOREIGN PATENT DOCUMENTS

| JP | 53-44539 | 4/1978 |
|----|----------|--------|
| JP | 08-137107 | 5/1996 |
| JP | 2000-131848 | 5/2000 |
| WO | WO 2003/107093 A2 | 12/2003 |
| WO | WO 2003/107093 A3 | 12/2003 |

OTHER PUBLICATIONS

Migulin, Vasily A. et al., "Adamantane-Based Crystals with Rhythmic Morphologies", Langmuir, vol. 17, No. 5, pp. 1324 to 1327, Jan. 18, 2001.
Dang et al, "Radical-chain reductive alkylation of electron-rich alkenes mediated by silanes in the presence of thiols as polarity-reversal catalysts", J. Chem. Soc., Perkin Trans., 1, 1999, pp. 2061-2068.
Database CA (online) Chemical Abstracts Service, Columbus, OH, USA, XP-002378848-2000:313534-Abstract.

* cited by examiner

*Primary Examiner*—Bernard Dentz
(74) *Attorney, Agent, or Firm*—Oblon, Spivak, McClelland, Maier & Neustadt, P.C.

(57) ABSTRACT

Provided are a novel halogenoacetoxyadamantane derivative which is useful as a modifying agent for a resin for a photoresist and a dry etching resistance-improving agent in the photolithography field, agricultural and medical intermediates and a compound for other various industrial products and a process for producing the same. To be specific, provided are a halogenoacetoxyadamantane derivative having a halogenoacetoxy group in an adamantane skeleton and a process for producing a halogenoacetoxyadamantane derivative, comprising the step of reacting a hydroxyl group of an adamantane skeleton with halogenoacetic halide or reacting the above hydroxyl group with a lithiation agent to derive it into a lithiumoxy group and then reacting halogenoacetic halide to introduce a halogenoacetoxy group.

11 Claims, No Drawings

HALOGENOACETOXYADAMANTANE DERIVATIVES AND PROCESS FOR PRODUCTION THEREOF

CROSS REFERENCES TO RELATED APPLICATIONS

This application is a national stage application of International Patent Application No. PCT/JP03/05442, filed on Apr. 28, 2003, and claims priority to Japanese Patent Application No. 2002-136183, filed on May 10, 2002, both of which are incorporated herein by reference in their entireties.

TECHNICAL FIELD

The present invention relates to a novel halogenoacetoxyadamantane derivative and a process for producing the same. More specifically, the present invention relates to a novel halogenoacetoxyadamantane derivative which is useful as a modifying agent for a resin for a photoresist and a dry etching resistance-improving agent in the photolithography field, agricultural and medical intermediates and a compound for other various industrial products and a process for efficiently producing the same.

BACKGROUND ART

It is known that adamantane is a compound which has a structure in which four cyclohexane rings are condensed in a cage form and which is highly symmetric and stable and that the derivatives thereof are useful as a medical raw material and a raw material for high functional industrial materials since it shows a specific function. For example, it has an optical characteristic and a heat resistance, so that it is tried to be used for an optical disc substrate, an optical fiber and a lens (refer to, for example, Japanese Patent Application Laid-Open No. 305044/1994 and Japanese Patent Application Laid-Open No. 302077/1997).

Further, adamantane esters are tried to be used as a resin raw material for a photoresist making use of an acid sensitivity, a dry etching resistance and a UV ray transmittance thereof (refer to, for example, Japanese Patent Application Laid-Open No. 39665/1992).

On the other hand, as a semiconductor element is progressively fined in recent years, it is required to be further fined at a lithography step in the production thereof, and therefore investigated are various methods for forming fine patterns using photoresist materials corresponding to irradiated beams having a short wavelength such as KrF, ArF and $F_2$ eximer laser beams. A novel photoresist material which can correspond to irradiated beams having a short wavelength such as the eximer laser beam and the like described above has been desired to be developed.

On the other hand, a halogenoacetoxyadamantane derivative which is an ester compound of adamantanol and halogenoacetic acid has an adamantane skeleton in a molecule, and it is considered to be useful as a modifying agent for a resin for a photoresist and agricultural and medical intermediates, but it is a compound which has not so far been known.

DISCLOSURE OF THE INVENTION

In light of the situations described above, an object of the present invention is to provide a novel adamantane derivative which is useful as a modifying agent for a resin for a photoresist and a dry etching resistance-improving agent in the photolithography field, agricultural and medical intermediates and a compound for other various industrial products.

Intensive researches repeated by the present inventors in order to develop a novel adamantane derivative which is useful for the uses described above have resulted in finding that a halogenoacetoxyadamantane derivative in which a halogenoacetoxy group is introduced into an adamantane skeleton is a novel compound which is not described in documents and can meet the object described above and that the above compound can efficiently be produced by a specific process. The present invention has been completed based on such knowledge.

That is, the present invention provides:

(1) a halogenoacetoxyadamantane derivative characterized by having a halogenoacetoxy group in an adamantane skeleton, (2) the halogenoacetoxyadamantane derivative as described in the above item (1), wherein the halogenoacetoxy group is a chloroacetoxy group or a bromoacetoxy group, (3) the halogenoacetoxyadamantane derivative as described in the above item (1) or (2), wherein it is 2-halogenoacetoxyadamantane, 2-alkyl-2-halogenoacetoxyadamantane, 1-halogenoacetoxyadamantane, 1-halogenoacetoxy-3-hydroxyadamantane, 1,3-bis(halogenoacetoxy)adamantane or 1-halogenoacetoxyperfluoroadamantane, (4) the halogenoacetoxyadamantane derivative as described in the above item (3), wherein it is 2-alkyl-2-halogenoacetoxyadamantane, (5) the halogenoacetoxyadamantane derivative as described in the above item (3), wherein it is 1-halogenoacetoxy-3-hydroxyadamantane and (6) a process for producing a halogenoacetoxyadamantane derivative, comprising the step of reacting a hydroxyl group of an adamantane skeleton with halogenoacetic halide or reacting the above hydroxyl group with a lithiation agent to derive it into a lithiumoxy group and then reacting halogenoacetic halide therewith to introduce a halogenoacetoxy group.

BEST MODE FOR CARRYING OUT THE INVENTION

The halogenoacetoxyadamantane derivative of the present invention is a novel compound which has a halogenoacetoxy group in an adamantane skeleton and which is not described in documents, and it can include, for example, compounds represented by Formulas (I-a), (I-b) and (I-c):

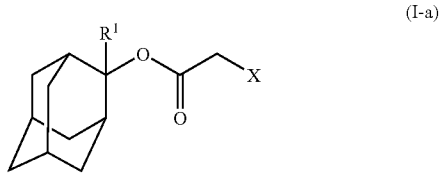

(I-a)

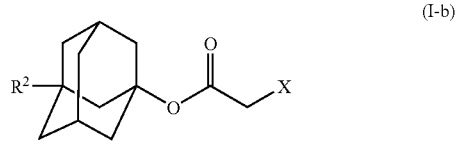

(I-b)

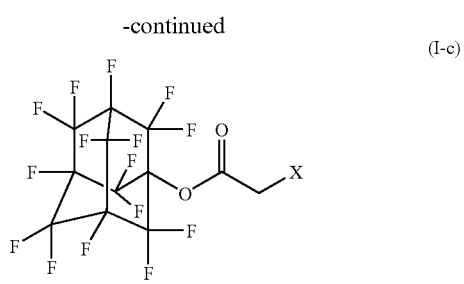

(I-c)

wherein R¹ represents a hydrogen atom or an alkyl group having 1 to 10 carbon atoms; R² represents a hydrogen atom, a hydroxyl group or a $CH_2COO-$ group; and X represents a halogen atom.

In Formula (I-a) described above, the alkyl group having 1 to 10 carbon atoms out of those represented by R¹ may be either linear or branched, and a lower alkyl group having 1 to 5 carbon atoms is particularly preferred. The examples of the above alkyl group includes methyl, ethyl, n-propyl, isopropyl, various butyls and various pentyls.

In Formulas (I-a), (I-b) and (I-c), the halogen atom represented by X includes fluorine, chlorine, bromine and iodine, and among them, chlorine and bromine are preferred.

The halogenoacetoxyadamantane derivative represented by Formula (I-a) described above is 2-halogenoacetoxyadamantane or 2-alkyl-2-halogenoacetoxyadamantane; the halogenoacetoxyadamantane derivative represented by Formula (I-b) is 1-halogenoacetoxyadamantane, 1-halogenoacetoxy-3-hydroxyadamantane or 1,3-bis(halogenoacetoxy)adamantane; and the halogenoacetoxyadamantane derivative represented by Formula (I-c) is 1-halogenoacetoxyperfluoroadamantane. In the present invention, among the above halogenoacetoxyadamantane derivatives, 2-alkyl-2-halogenoacetoxyadamantane and 1-halogenoacetoxy-3-hydroxyadamantane can preferably be given. The specific examples of the above 2-alkyl-2-halogenoacetoxyadamantane include 2-chloroacetoxy-2-methyladamantane, 2-bromoacetoxy-2-methyladamantane and 2-chloroacetoxy-2-ethyladamantane. Further, the specific examples of 1-halogenoacetoxy-3-hydroxyadamantane includes 1-bromoacetoxy-3-hydroxyadamantane.

The halogenoacetoxyadamantane derivatives described above can efficiently be produced by the process of the present invention shown below.

In the production process for the halogenoacetoxyadamantane derivative of the present invention, available are two embodiments, that is, (1) a process in which a hydroxyl group in an adamantane skeleton is reacted with halogenoacetic halide and (2) a process in which the hydroxyl group in the adamantane skeleton is reacted with a lithiation agent to derive it into a lithiumoxy group and in which halogenoacetic halide is then reacted therewith.

In the process (1) described above, adamantanols (II) and halogenoacetic halide (III) are subjected to esterification reaction according to a reaction equation (A):

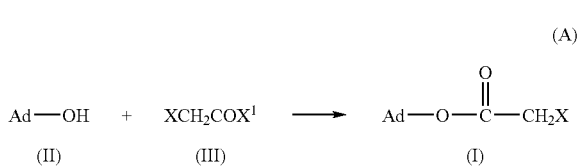

(A)

(wherein Ad is an adamantane ring which has or does not have a substituent; X¹ represents a halogen atom; and X is the same as described above), whereby the targeted halogenoacetoxyadamantane derivative (I) is obtained. When the adamantanols (II) have plural hydroxyl groups in a molecule, the halogenoacetic halide (III) can be reacted with a part or the whole of the hydroxyl groups.

In the above reaction, the adamantanols (II) used as one of the raw materials can include, for example, 2-adamantanol and 2-alkyl-2-adamantanol as a raw material for the compound represented by Formula (I-a) described above, 1-adamantanol and 1,3-adamantanediol as a raw material for the compound represented by Formula (I-b) and perfluoro-1-adamantanol as a raw material for the compound represented by Formula (I-c).

The halogenoacetic halide (III) which is used as another raw material includes, for example, monochloroacetic chloride, monochloroacetic fluoride, monochloroacetic bromide, monobromoacetic chloride, monobromoacetic fluoride and monobromoacetic bromide.

The above reaction can be carried out using a basic catalyst in the presence or absence of a solvent. The above basic catalyst is preferably, for example, an organic base such as trimethylamine, triethylamine, pyridine, N,N-dimethylaminopyridine and N,N-dimethylaniline, and they may be used alone or in combination of two or more kinds thereof. When the solvent is used, the above solvent includes, for example, halogenated hydrocarbon base solvents such as dichloromethane, chloroform, carbon tetrachloride and 1,2-dichloroethane, ether base solvents such as diethyl ether, tetrahydrofuran and dioxane, aliphatic hydrocarbon base solvents such hexane, heptane and octane and aromatic hydrocarbon base solvents such benzene, toluene and xylene. The above solvents may be used alone or in a mixture of two or more kinds thereof.

The reaction temperature is selected in a range of usually −78 to 100° C., preferably −78 to 80° C. The reaction pressure is selected in a range of usually 0.1 to 10 MPa. The reaction time is influenced by the conditions such as the reaction temperature and the like and can not definitely be determined, and it is usually one hour to 10 days, preferably one hour to 3 days. The concentration of the raw materials in using the solvent may be optional and shall not specifically be restricted as long as it is not higher than a saturation solubility, and it is preferably 0.5 to 1.0 mole/liter.

On the other hand, in the process (2) described above, a lithiation agent is reacted with the adamantanols (II) according to a reaction equation (B):

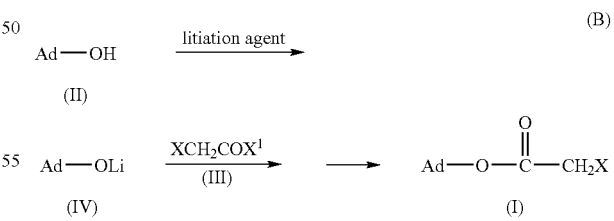

(B)

(wherein Ad, X and X¹ are the same as described above) to derive them into lithium adamantyl oxides (IV), and then the halogenoacetic halide (III) is reacted therewith, whereby the targeted halogenoacetoxyadamantane derivative (I) is obtained. When the adamantanols (II) have plural hydroxyl groups in a molecule, the lithiation agent can be reacted with a part or the whole of the hydroxyl groups, and then the halogenoacetic halide (III) can be reacted therewith.

In the above reaction, the adamantanols (II) used as one of the raw materials include the same ones as explained in the process (1) described above. The lithium adamantyl oxides (IV) corresponding to them include lithium 2-adamantyl oxide, lithium 2-alkyl-2-adamantyl oxide, lithium 1-adamantyl oxide, dilithium 1,3-adamantyl dioxide and lithium perfluoroadamantyl oxide. Also, the lithiation agent includes, for example, lithium metal, n-butyllithium, sec-butyllithium and tert-butyllithium.

The halogenoacetic halide (III) used as another raw material includes the same ones as explained in the process (1) described above.

The lithium adamantyl oxides (IV) are reacted with the halogenoacetic halide (III) in the presence of a solvent. The above solvent includes, for example, ether base solvents such as diethyl ether, tetrahydrofuran and dioxane, aliphatic hydrocarbon base solvents such hexane, heptane and octane and aromatic hydrocarbon base solvents such benzene, toluene and xylene. The above solvents may be used alone or in a mixture of two or more kinds thereof.

The reaction temperature is selected in a range of usually −78 to 100° C., preferably −78 to a room temperature. The reaction pressure is selected in a range of usually 0.1 to 10 MPa (G). The reaction time is influenced by the conditions such as the reaction temperature and the like and can not definitely be determined, and it is usually one hour to 10 days, preferably one hour to 3 days. The concentration of the raw materials may be optional and shall not specifically be restricted as long as it is not higher than a saturation solubility, and it is preferably 0.5 to 1.0 mole/liter.

The halogenoacetoxyadamantane derivative of the present invention can efficiently be produced in the manners described above.

The compounds thus obtained can be identified by means of gas chromatography (GC), liquid chromatography (LC), gas chromatography and mass spectroscopy (GC-MS), nuclear magnetic resonance spectroscopy (NMR), infrared spectroscopy (IR) and a melting point-measuring device.

EXAMPLES

Next, the present invention shall be explained in further details with reference to examples, but the present invention shall by no means be restricted by these examples. All operations of feeding through after-treatment and storage were carried out under nitrogen flow to prevent penetration of moisture.

Example 1

Production of 2-chloroacetoxy-2-methyladamantane

A 100 ml vessel equipped with a three-way cock was charged with 4.67 g (28.1 millimole) of 2-methyl-2-adamantanol and 2.83 ml (35.0 millimole) of pyridine, and 30 ml of dried tetrahydrofuran was further added to dissolve them. Then, a tetrahydrofuran solution containing 4.42 g (39.2 millimole) of chloroacetic chloride was dropwise added to the above solution by means of a cannula in about 15 minutes under cooling with ice. Further, chloroacetic chloride remaining in the vessel was washed with 10 ml of tetrahydrofuran and joined to the solution. Reaction was carried out at a room temperature for about 24 hours, and then 300 ml of water was added to the reaction liquid to terminate the reaction.

Next, the reaction mixture thus obtained was washed three times with water and then extracted three times with 100 ml of diethyl ether, and the extract was dried on anhydrous sodium sulfate. Next, the extract was concentrated and then separated and refined by means of a column (silica was filled therein, and a hexane/diethyl ether mixed solvent (volume ratio 10:1) was used as a developing liquid) to obtain 5.89 g (20.5 millimole) of a white solid matter of 2-chloroacetoxy-2-methyladamantane (yield: 72.8 %).

The spectral data are shown below.

Nuclear magnetic resonance spectroscopy (NMR): $CDCl_3$
$^1$H-NMR (270 MHz): 1.57–2.31 (m, 12H), 1.65 (s, 3H), 4.02 (s, 2H)
$^{13}$C-NMR (68MHz): 22.37, 26.62, 27.30, 32.97, 34.56, 36.18, 38.06, 41.95, 89.82, 165.69

Example 2

Production of 2-bromoacetoxy-2-methyladamantane

A 100 ml vessel equipped with a three-way cock was charged with 2.51 g (15.1 millimole) of 2-methyl-2-adamantanol and 1.62 ml (20.0 millimole) of pyridine, and 30 ml of dried tetrahydrofuran was further added to dissolve them. Then, a tetrahydrofuran solution containing 6.01 g (30.2 millimole) of bromoacetic bromide was dropwise added to the above solution by means of a cannula in about 15 minutes under cooling with ice. Further, bromoacetic bromide remaining in the vessel was washed with 10 ml of tetrahydrofuran and joined to the solution. Reaction was carried out at a room temperature for about 24 hours, and then 300 ml of water was added to the reaction liquid to terminate the reaction.

Next, the reaction mixture thus obtained was washed three times with water and then extracted three times with 100 ml of diethyl ether, and the extract was dried on anhydrous sodium sulfate. Next, the extract was concentrated and then separated and refined by means of a column (silica was filled therein, and a hexane/diethyl ether mixed solvent (volume ratio 10:1) was used as a developing liquid) to obtain 0.61 g (2.12 millimole) of a pale yellow solid matter of 2-bromoacetoxy-2-methyladamantane (yield: 14%).

The spectral data are shown below.

Nuclear magnetic resonance spectroscopy (NMR): $CDCl_3$
$^1$H-NMR (270 MHz): 1.55–2.30 (m, 12H), 1.63 (s, 3H), 3.80 (s, 2H)
$^{13}$C-NMR (68 MHz): 21.97, 26.49, 26.99, 32.77, 34.41, 35.99, 37.92, 65.03, 89.28, 165.32

Example 3

Production of 2-ethyl-2-adamantyl chloroacetate (2-chloroacetoxy-2-ethyladamantane)

A 50 ml vessel equipped with a three-way cock was charged with 1.00 g (5.55 millimole) of 2-ethyl-2-adamantanol and 7.2 ml (8.90 millimole) of pyridine, and 30 ml of dried tetrahydrofuran was further added to dissolve them. Then, a tetrahydrofuran solution containing 0.96 ml (12.0 millimole) of chloroacetic chloride was dropwise added to the above solution by means of a cannula in about 15 minutes under cooling with ice. Further, chloroacetic chloride remaining in the vessel was washed with 10 ml of tetrahydrofuran and joined to the solution. Reaction was carried out at a room temperature for about 24 hours, and then 300 ml of water was added to the reaction liquid to terminate the reaction.

Next, the reaction mixture thus obtained was washed three times with water and then extracted three times with 50 ml of diethyl ether, and the extract was dried on anhydrous sodium sulfate. Next, the extract was concentrated and then separated and refined by means of a column (silica was filled therein, and a hexane/diethyl ether mixed solvent (volume ratio 10:1) was used as a developing liquid) to obtain 0.316 g (1.23 millimole) of a white solid matter of 2-ethyl-2-adamantyl chloroacetate (yield: 22.2%).

The spectral data are shown below.

Nuclear magnetic resonance spectroscopy (NMR): $CDCl_3$ $^1$H-NMR (270 MHz): 0.81 (t, J=7.29, 3H), 1.57–2.39 (m, 14H), 2.20 (q, J=7.29, 2H), 4.04 (s, 2H)

$^{13}$C-NMR (68MHz): 6.74, 24.76, 27.02, 32.98, 33.45, 34.02, 38.09, 41.62, 91.80, 165.32 (C=O)

Example 4

Production of 3-hydroxy-1-adamantyl bromoacetate (1-bromoacetoxy-3-hydroxyadamantane)

A 200 ml vessel equipped with a three-way cock was charged with 0.673 g (4.00 millimole) of 1,3-adamantanediol and 4.37 ml (5.40 millimole) of pyridine, and 100 ml of dried dioxane was further added, followed by hating the solution up to 95° C. Then, this solution was cooled down to 50° C., and a dioxane solution containing 0.35 ml (4.00 millimole) of bromoacetic bromide was added thereto by means of a cannula. Reaction was carried out at a room temperature for about 24 hours, and then 300 ml of water was added to the reaction liquid to terminate the reaction.

Next, the reaction mixture thus obtained was washed three times with water and then extracted three times with 30 ml of diethyl ether, and the extract was dried on anhydrous sodium sulfate. Next, the extract was concentrated and then separated and refined by means of a column (silica was filled therein, and a hexane/diethyl ether mixed solvent (volume ratio 10:1) was used as a developing liquid) to obtain 0.15 g (0.519 millimole) of a white solid matter of 3-hydroxy-1-adamantyl bromoacetate (yield: 13.0%).

The spectral data are shown below.

Nuclear magnetic resonance spectroscopy (NMR): $CDCl_3$ $^1$H-NMR (270 MHz): 1.54–2.45 (m, 14H), 3.28 (br, 1H), 3.76 (s, 2H)

$^{13}$C-NMR (68 MHz): 31.12 ($CH_2$), 34.51, 39.56, 43.69, 48.59, 70.31 (C), 82.69 ($CH_2$), 83.35 (C), 165.71 (C=O)

INDUSTRIAL APPLICABILITY

The halogenoacetoxyadamantane derivative of the present invention is a novel compound and is useful as a modifying agent for a resin for a photoresist and a dry etching resistance-improving agent in the photolithography field, agricultural and medical intermediates and a compound for other various industrial products.

What is claimed is:

1. A halogenoacetoxyadamantane derivative which is 1-halogenoacetoxyperfluoroadamantane.

2. A halogenoacetoxyadamantane derivative which is 2-alkyl-2-halogenoacetoxyadamantane.

3. A halogenoacetoxyadamantane which is 1-halogenoacetoxy-3-hydroxyadamantane.

4. A process for producing a halogenoacetoxyadamantane derivative, comprising:
   reacting a hydroxyl group of an adamantane skeleton directly with halogenoacetic halide or reacting said hydroxyl group with a lithiation agent to obtain a lithiumoxy group and then reacting halogenoacetic halide therewith to introduce a halogenoacetoxy group;
   wherein said halogenoacetoxyadamantane derivative is 2-alkyl-2-halogenoacetoxyadamantane, 1-halogenoacetoxy-3-hydroxyadamantane or 1-halogenoacetoxyperfluoroadamantane.

5. The process of claim 4, wherein said lithiating agent is lithium metal, n-butyllithium, sec-butyllithium or tert-butyllithium.

6. A photoresist composition, comprising:
   the halogenoacetoxyadamantane derivative of claim 1.

7. A photoresist composition, comprising:
   the halogenoacetoxyadamantane derivative of claim 2.

8. A photoresist composition, comprising:
   the halogenoacetoxyadamantane derivative of claim 3.

9. A dry-etching resistance improving agent, comprising:
   the halogenoacetoxyadamantane derivative of claim 1.

10. A dry-etching resistance improving agent, comprising:
    the halogenoacetoxyadamantane derivative of claim 2.

11. A dry-etching resistance improving agent, comprising:
    the halogenoacetoxyadamantane derivative of claim 3.

* * * * *